United States Patent
Carnahan

(10) Patent No.: US 11,597,710 B2
(45) Date of Patent: *Mar. 7, 2023

(54) SOLVENT-FREE THCA EXTRACTION PROCESS

(71) Applicant: Tresvertol Inc., Waterloo (CA)

(72) Inventor: Jay Carnahan, Ontario (CA)

(73) Assignee: Tresvertol Inc., Waterloo (CA)

( * ) Notice: Subject to any disclaimer, the term of this patent is extended or adjusted under 35 U.S.C. 154(b) by 55 days.

This patent is subject to a terminal disclaimer.

(21) Appl. No.: 17/388,343

(22) Filed: Jul. 29, 2021

(65) Prior Publication Data

US 2021/0355096 A1    Nov. 18, 2021

Related U.S. Application Data

(63) Continuation of application No. 16/612,983, filed as application No. PCT/CA2018/000097 on May 15, 2018, now Pat. No. 11,098,023.

(60) Provisional application No. 62/508,055, filed on May 18, 2017.

(30) Foreign Application Priority Data

Dec. 7, 2017 (CA) ................................. CA 2987979

(51) Int. Cl.

| C07D 311/74 | (2006.01) |
| A23L 33/00 | (2016.01) |
| A23P 10/22 | (2016.01) |
| A23L 33/105 | (2016.01) |
| A23L 33/115 | (2016.01) |
| A23P 30/20 | (2016.01) |
| A61K 31/352 | (2006.01) |
| A61K 47/44 | (2017.01) |

(52) U.S. Cl.
CPC .......... *C07D 311/74* (2013.01); *A23L 33/105* (2016.08); *A23L 33/115* (2016.08); *A23L 33/30* (2016.08); *A23P 10/22* (2016.08); *A23P 30/20* (2016.08); *A61K 31/352* (2013.01); *A61K 47/44* (2013.01); *A61K 2236/30* (2013.01)

(58) Field of Classification Search
None
See application file for complete search history.

(56) References Cited

U.S. PATENT DOCUMENTS

| 6,403,126 | B1 | 6/2002 | Webster et al. |
| 9,199,960 | B2 | 12/2015 | Ferri |
| 9,732,009 | B2 | 8/2017 | Raber et al. |
| 2004/0147767 | A1 | 7/2004 | Whittle et al. |
| 2010/0168448 | A1 | 7/2010 | Flockhart et al. |
| 2012/0095087 | A1 | 4/2012 | Hyatt |
| 2015/0152018 | A1 | 6/2015 | Raber et al. |
| 2016/0106705 | A1 | 4/2016 | Verzura et al. |
| 2016/0213720 | A1 | 7/2016 | Barringer |

FOREIGN PATENT DOCUMENTS

WO    2016187679 A1    12/2016

OTHER PUBLICATIONS

<https://skunkpharmresearch.com/extracting-with-oils-and-fats/> Extracting With Oils Skunk Pharm Research. Mar. 16, 2012, 4 pages.
Romano, et al., "Cannabis oil: chemical evaluation of an upcoming cannabis-based medicine", Cannabinoids 1(1), 2013, pp. 1-11.
Russo, Taming THC: potential cannabis synergy and phytocannabinoid-terpenoid entourage effects:, British Journal of Pharmacology, Aug. 2011, 163(7): 1344-1364. doi: 10.1111/j. 1476-5381.2011.01238.x PMCID:PMC3165946, 21 pages.
International Search Report dated Aug. 8, 2018 in PCT Application No. PCT/CA2018/000097, filed on May 15, 2018, 3 pages.

*Primary Examiner* — Michael V Meller
(74) *Attorney, Agent, or Firm* — Berg Hill Greenleaf Ruscitti LLP

(57) ABSTRACT

A solvent-free method to extract THCA from cannabis, said method comprising: providing a source of THCA-containing cannabis plant; providing a source of natural oil; combining said source of THCA-containing cannabis and said source of natural oil into a blend; milling said blend; optionally, heating the blend during the milling; and extracting a THCA-containing liquid generated during the milling.

1 Claim, 4 Drawing Sheets

Entourage Plus Process Workflow
| Collect seeds and trichome plant material |
| Select supplementary edible material |
| Mix plant material with edible material |
↓
| Place mixture into preheated separation machine |
| Increase temperature to 180 degrees F |
↓
| Increase pressure to 150- 200psi |
| Collect byproducts of Entourage Plus |
Figure 1

Byproducts of Entourage Plus Process a.

Cannabinoid/terpene infused oil material – edible cannabis oil b.

Cannabinoid/terpene infused fibrous material – edible cannabis protein powder c.

Cannabinoid/terpene infused paste material – edible cannabis protein paste

Figure 2

Phytochemical Profile of Entourage Plus

| PHYTOCANNABINOIDS (before and after extrusion) |
| --- |
| ^ 9 Tetrahydrocannabidiol (THC) |
| ^ 8 Tetrahydrocannabidiol (D8 THC) |
| (THCA) pre decarb |
| Cannabidiol (CBD) |
| (CBDA) pre decarb |
| Cannabigerol (CBG) |
| Cannabigerolic acid (CBGa) |
| Cannabichromene (CBC) |
| Tetrahydrocannabiverian (THCV) |
| Cannabivarian (CBDV) |
| Cannabinol (CBN) |

| TERPENOIDS (FLAVONOIDS) (ESSENTIAL OIL) (before and after separation) |
| --- |
| Limonene (also found in lemon) |
| a-Pinene (also found in pine needles) |
| Myrcene (also found in hops) |
| Linalool (also found in lavender, cilantro) |
| Caryophyllene Oxide (also found in lemon balm) |
| Beta-caryophyllene (also found in Echinacea) |
| Phytol (also found in green tea) |
| Nerolidol (also found in orange) |

| ESSENTIAL FATTY ACIDS |
| --- |
| α-Linolenic acid (ALA) omega 3 |
| Trans α-Linolenic acid (ALA) omega 3 |
| Linoleic acid (LA) omega 6 |
| Trans Linoleic acid (LA) omega 6 |
| beta linoleic acid omega 6 |

OTHER POTENTIAL COMPONENTS: sesquiterpenes, terpenes, cannabinoids, flavonoids, pigments, sugars, chlorophyll, waxes, lignin, pectin, starches, cellulose

Figure 3 ial United States, which PCT application claimed the benefit# SOLVENT-FREE THCA EXTRACTION PROCESS

CROSS REFERENCE TO RELATED APPLICATION

This application is a continuation of U.S. application Ser. No. 16/612,983, filed Nov. 12, 2019; which is a national stage application under 35 U.S.C. 371 and claims the benefit of PCT Application No. PCT/CA2018/000097 having an international filing date of May 15, 2018, which designates the United States, which PCT application claimed the benefit of Canadian Application No. 2,987,979, filed Dec. 7, 2017, which claimed the benefit of U.S. Application Ser. No. 62/508,055, filed May 18, 2017, all of which are incorporated by reference in their entirety.

FIELD OF THE INVENTION

The present invention relates generally to a method of extracting THCA from the cannabis plant, more specifically it involves a novel solvent-free extraction process and formulation for manufacturing edible foodstuffs and orally delivered medicine.

BACKGROUND OF THE INVENTION

The use of medicinal plants has been a known part of human civilization since its inception. Prior to the advent of modern medicine, so-called "natural" remedies were widely used as treatments for numerous maladies. While modern medicine has given humanity effective treatments for many previously incurable conditions with the benefit of herbal and botanical cures cannot be overlooked. The effectiveness of botanical medicines only becomes more important as individuals develop sensitivities or allergies to allopathic medicine.

Since modern medications are targeted for a specific problem and utilizes only isolates of single-molecule "active medicinal ingredients" they do not target overall health. Botanical medications, being part of our natural adaptation to our environment and the human evolution in the beneficial utilization of their components, very often do promote whole-body health. This reductionist mentality, adopted widely from processing to patient, creates many steps, takes time, destroys synergistic constituents and creates unnecessary waste streams.

There are a number of known processes used or said to be useful for the extraction of chemicals from plants, below are some which cover a range of techniques.

U.S. Pat. No. 9,732,009 B2 discloses a process for purifying one or more chemical constituents from plant matter using extraction with a fluid that is not a solvent, for example, with a vegetable oil. It is stated that the extracted chemical constituents may then optionally be further processed by heating in order to induce desired chemical transformations. The extracted chemical constituents are also processed by concentrating at reduced pressure, for example, by distillation.

US patent application no. 2004/0147767 A1 discloses a process for preparing extracts of natural products such as plant material, and for preparing purified extracts from crude extracts of natural products, by extraction with hot gas. It claims a process for preparing a cannabinoid-rich extract from cannabis plant material or a primary extract thereof loaded onto an inert matrix material, comprising contacting the cannabis plant material or primary solvent extract with a heated gas at a temperature which is greater than 100° C. and sufficient to volatilise one or more cannabinoids but does not cause pyrolysis of the cannabis plant material or primary solvent extract thereby volatising one or more cannabinoids to form a vapour, and condensing the vapour to form an extract rich in cannabinoids.

US patent application 2012/0095087 A1 discloses a process for producing a composition with bioactive and/or bioavailable Cannabis-derived cannabinoids known to be effective for CB1 and/or CB2 modulation, and a plurality of indications for patients in need. Using a heat cycle process to combine cannabinoids, including but not limited to THC and CBD with flax seed oil and at least one of the triglycerides therein, an extract is formulated which enables substantially profiled and Cannabinoid ratio-balanced aliquots ("miquots") to be offered for consideration to patients, including non-psychoactive topically and orally delivered products and systems.

U.S. Pat. No. 9,199,960 B2 discloses a method and associated system of treating a plant material consisting essentially of the plant cannabis in order to extract cannabinoids in liquid form from the plant material. The method is said to include heating the plant material; drying the plant material; grinding the dried plant material into a powder form; marinating the dried plant powder in a solvent for a predetermined time period to form a marinated mixture; shaking and heating the marinated mixture; filtering the mixture so that only a liquid part of the mixture remains; and evaporating from the liquid the solvent in order to provide the cannabinoid liquid extract.

US patent application no. 2010/0168448 A1 discloses a method of preparing cannabinoids in substantially pure form starting from plant material. Also described are substantially pure preparations of various cannabinoids and cannabinoid acids, and also extracts enriched in cannabinoids and cannabinoid acids. More specifically it claims a method of obtaining a substantially pure cannabinoid or cannabinoid acid or a product enriched in a given cannabinoid or cannabinoid acid from a plant material, comprising: i) obtaining an extract containing a cannabinoid or cannabinoid acid from a plant material; ii) subjecting the extract of step (i) to a chromatographic step to produce a partially purified extract; iii) dissolving the partially purified extract in a first solvent, removing any insoluble material therefrom and removing the solvent; and iv) dissolving the product obtained in step iii) in a second solvent, removing any insoluble material therefrom, and removing the solvent to obtain the substantially pure cannabinoid or cannabinoid acid or the product enriched in a given cannabinoid or cannabinoid acid, wherein the first and second solvents are different, and wherein one of the first or second solvents is a solvent which is substantially more polar than the cannabinoid/cannabinoid acid which it is desired to purify, and the other solvent is a solvent which is substantially less polar than the cannabinoid/cannabinoid acid which it is desired to purify.

U.S. Pat. No. 6,403,126 B1 discloses a method of extracting cannabinoids, cannflavins, and/or essential oils from hemp and/or of producing a whole hemp extract lacking $\Delta^9$-THC is herein described. The industrial hemp is harvested and the chaff is threshed from the seeds. The chaff is then ground and the ground chaff is extracted with an organic solvent. The extract is then loaded onto a chromatographic column selected to fractionate specific cannabinoids, cannflavins, and essential oils. In one embodiment, $\Delta^9$-THC is fractionated out of the extract, producing a whole hemp extract lacking $\Delta^9$-THC. In other embodiments, specific cannabinoids and related compounds of interest are fractionated out, thereby producing purified cannabinoids, cannflavins, and related compounds.

Despite the number of available processes known, there still exists a need for a better process which lacks some of the more extreme conditions used in known processes or avoids the use of solvents which affect the final product.

The "Entourage Effect" is well known through Dr. Raphael Mechoulam's and Ethan Russos's research. "*E. Russo's Taming THC: potential cannabis synergy and phytocannabthoid-terpenoid entourage effects Br J Pharmacol.* 2011 August; 163(7): 1344-1364. doi: 10.11141476-5381.2011.01238.x PMCID: PMC3165946", describes how an ensemble of phytochemicals and essential oils, also known as terpenes, works better than THC alone. Without terpenes, flavonoids and other natural phytochemicals, THC alone lacks the desired effects.

This one-step processing technology preserves terpenoids and cannabinoids from decarboxylation and infuses essential fatty acids from flax seed and/or hemp seed into a high-yield, dose-specific cannabis oil derivative. Seed, nut or bean with flower\leaf combined in the correct formulation using this singular extraction method produce an oil derivative as well as protein powder and paste\butter byproduct that is precise, reliable, and efficient for commercial production.

SUMMARY OF THE INVENTION

The present invention is a marked improvement over the known entourage effect and further combines the variable of the cannabis seed. The science of the flower combined with the seed has not been explored in processing constituents and effects. Analysis of the flower as it grows in a natural state would show large amount of seed presence. Seed in flower has been eliminated from recreational marijuana market. The seed is seen as a contaminant to smoking applications in consumption. Commercial cultivators and processors fail to acknowledge the importance of the seed in human neurological delivery. Science has focussed on the female cannabis flower that is void of the seed. This as a gross oversight in the emerging international cannabis industry. The science of the seed and the flowers effect together in extraction is known as Entourage Plus.

The Entourage Plus Process takes the cannabinoids and terpenes (see FIG. 3) and infuses them in a colloid of essential fatty acids that optimizes absorption in neural cells. This also provides raw, nutritive and efficacious "carrier" materials for the beneficial components.

The products obtained are not for the recreational market as the byproducts do not have high amounts of the psychoactive molecule Δ 9THC. The process of the present invention allows one to make edibles, orals, transdermal applications, infused with therapeutic compounds producing superior quality "uncut" raw materials for the natural, medicinal and/or nutraceutical products industries. It makes use of the array of therapeutic properties of cannabis flowers/leaves and seeds to aid in promoting the overall health and wellness of an individual. An example of preserving terpenoids; Beta-caryophyllene, for example, is a sesquiterpene found in the essential oil of black pepper, oregano, and other edible herbs, as well as in various cannabis strains and in many green, leafy vegetables. It is gastro-protective, good for treating certain ulcers, and offers great promise as a therapeutic compound for inflammatory conditions and auto-immune disorders because it binds directly to the peripheral cannabinoid receptor known as "CB2."

Because the process uses relatively low temperatures, the CBGA, CBDA, THCA components remain in a raw state, and terpenoids—volatile aromatic oils lost in other extraction processes—are preserved.

Among them are monoterpenes, diterpenes, and sesquiterpenes, which are characterized by the number of repeating units of a 5-carbon molecule called isoprene, the structural hallmark of all terpenoid compounds. The terpenes in marijuana have given the plant an enduring, evolutionary advantage. Pungent terpenoid oils repel insects and animal grazers; others prevent fungus.

Additionally, quantifiable amounts of THC, THCA, Δ 8THC and CBC are also infused within the materials produced. The seed oil, protein powder and paste\butter extract materials act as an excellent and nutritive carrier for the medicinal components. They can be consumed in their raw form as well as offering a wide versatility in further processing for the desired nutritive and medicinal end products.

Entourage Plus is useful for medical applications where it is critical to retain quantifiable levels of CBGA, THCA, CBDA, Omega 3, Omega 6, tocopherols, enzymes and other therapeutic components; as opposed to the recreational marijuana market that is primarily concerned with activating the psychoactive effects of decarboxylated THC. The process according to the present invention produces novel CBGA and Δ 8 molecules in concentrations that more than doubles the originating flower/trichome material. For example, 10% THCA Cannabis flower (pink star)=20 mg/ml THCA Cannabis oil. Another example, 0.097% CBGA Cannabis flower (pink star)=0.26 mg/ml CBGA Cannabis oil (depending upon formulation of flower and seed feedstock).

The process according to a preferred embodiment of the present invention is effective with *Cannabis ruderalis, sativa* and *indica*; pharmaceutical and non-pharmaceutical cultivars. Edibles can be created directly by combining the trichome mixture with bases such as hemp seeds, flax seeds, soy beans, cacao beans, chia seeds, nuts and other "superfoods." Byproducts of the process according to a preferred embodiment of the present invention that include protein/fibre and paste\butter can be consumed or added to other foods to create additional nutritive and therapeutic benefits.

According to an aspect of the present invention, there is provided a solvent-free method to extract THCA from cannabis, said method comprising:

providing a source of THCA-containing cannabis plant;
providing a source of natural oil;
combining said source of THCA-containing cannabis and said source of natural oil into a blend;
milling said blend;
optionally, heating the blend during the milling; and
extracting a THCA-containing liquid generated during the milling.

According to a preferred embodiment, the natural oil is selected from the group consisting of: flax seed oil; chia seed oil; hemp seed oil; sunflower seed oil; pumpkin seed oil; sesame seed oil; apricot kernel oil; apple seed oil; almond oil; walnut oil; pecan oil; brazil nut oil; cedar nut oil/pine nut oil; and cashew oil.

Preferably, the milling step is performed by mechanical extrusion. Preferably, the mechanical extrusion is performed by a screw auger. Preferably, the stream of THCA-containing pulp and fiber is recovered separately from the liquid.

According to another aspect of the present invention, there is provided a composition comprising a solvent-free THCA extract. Preferably, the composition is a pharmaceutical composition. Preferably also, the composition comprises a natural oil. Preferably, the natural oil is selected from the group consisting of: seed-based oils and nut-based oils.

Preferably, the seed-based oils are selected from the group consisting of: flax seeds; chia seeds; hemp seeds; sunflower seeds; pumpkin seeds; sesame seeds; apricot seeds; and apple seeds.

Preferably, the nut-based oil is selected from the group consisting of: almond; walnut; pecan; Brazil nut; cedar nut/pine nut; and cashew.

According to another aspect of the present invention, there is provided a use of a source of natural oil to extract THCA from a cannabis plant, wherein the extraction is performed using a screw auger.

According to another aspect of the present invention, there is provided a nutritional supplement comprising:
a solvent-free THCA extract; and
at least one natural oil selected from the group consisting of: flax seed oil; chia seed oil; hemp seed oil; sunflower seed oil; pumpkin seed oil; sesame seed oil; apricot seed oil; apple seed oil; almond oil; walnut oil; pecan oil; brazil nut oil; cedar nut oil/pine nut oil; and cashew oil.

Preferably, the supplement is in the form of seed oil, protein powder and paste\butter.

According to another aspect of the present invention, there is provided a medicinal dosage form comprising a solvent-free THCA extract.

Preferably, the medicinal formulation according to claim 16 wherein the formulation is in the form of an edible; a drink; a capsule; a tincture; a topical; a coffee; and a suppository.

According to another aspect of the present invention, there is provided a high-fibre, high-protein powder resulting from a solvent-free extraction of THCA from a cannabis plant, said powder comprising:
10 wt % essential fatty acids; and
0.2 wt % THCA/THC and/or CBDA/CBD.

BRIEF DESCRIPTION OF THE DRAWINGS

The present invention may be better understood in consideration of the following description of various embodiments of the invention in connection with the accompanying figures, in which:

FIG. 1 is a diagram illustrating the process according to a preferred embodiment of the present invention;

FIG. 2 is a diagram illustrating the byproducts that result from use of the present invention;

FIG. 3 is a diagram illustrating the phytocannabinoids and terpenes; and

DETAILED DESCRIPTION OF PREFERRED EMBODIMENTS OF THE INVENTION

Figure 4:
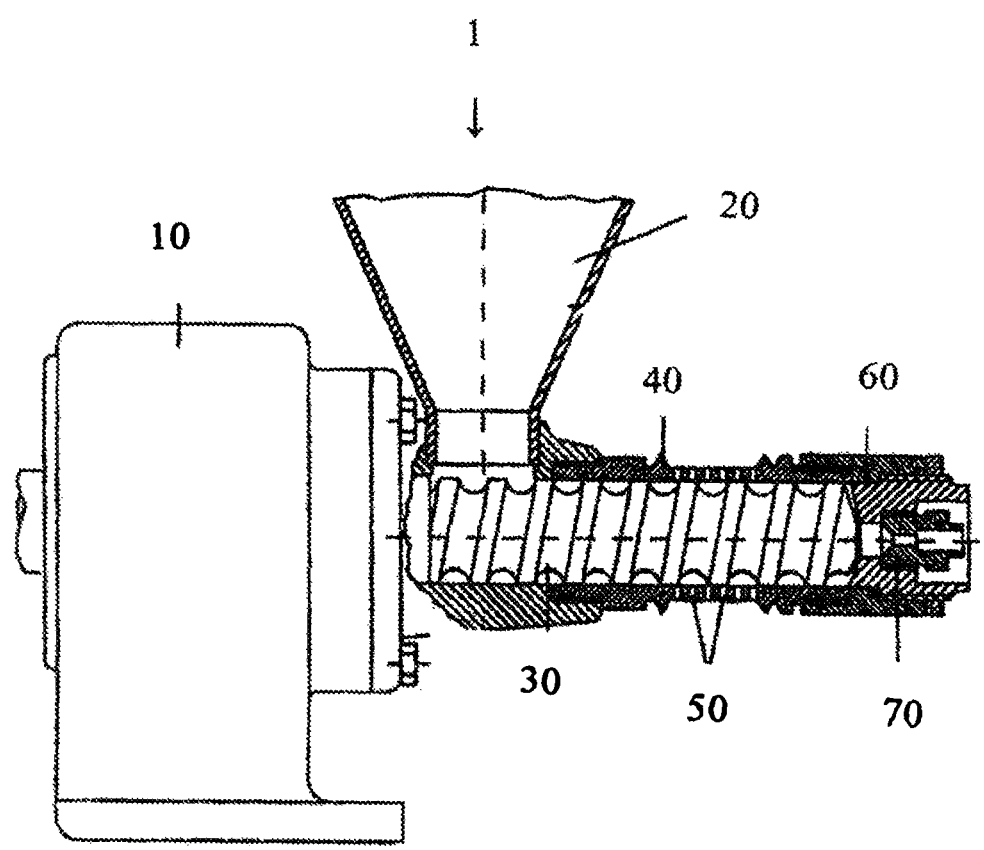
FIG. 4 is a side view of an extraction machine according to a preferred embodiment of the present invention.

The description that follows, and the embodiments described therein, is provided by way of illustration of an example, or examples, of particular embodiments of the principles of the present invention. These examples are provided for the purposes of explanation, and not limitation, of those principles and of the invention.

The process according to a preferred embodiment of the present invention is continuous and high-yielding, using a 5 kW motor at 20 amps for power, scalable by the addition of more separation machines. Technically competent operators can manipulate the one-step mechanical extraction to produce quantifiable medicinal concentrations for a standardized product. As illustrated in FIG. 3, the resulting infused medicinal cannabis oil is a dark colloid, rich in smell as it contains a wide array of terpenes, extremely strong and diverse tasting flavonoids. The resulting oil may be used orally or transdermally. The oil products are not intended for smoking, vaporizing or injecting.

Traditional extraction methods, including $CO_2$, alcohol, oil, butane, glycerine and water extraction, are much slower and require multiple steps that affect product uniformity with each step increasing the possibility of human error or production variations. Depending on the method, damage to cannabinoids, terpenes, flavonoids, essential fats, essential oils and enzymes is extremely likely. Dose control is a cannabis industry problem that can cause serious breaches of government regulations and is thought to jeopardize child safety. High concentrations of THCA/THC and/or CBDA/CBD are not permitted in finished consumer products. The process according to a preferred embodiment of the present invention is capable of producing a range of consistent, quantifiable and versatile extracts usable in its raw form.

By precise control of pressure, heat, and revolutions per minute, the process according to a preferred embodiment of the present invention can obtain consistent results of 30 mg/ml THCA content, the commonly accepted standard concentration of THCA/THC and/or CBDA/CBD medicine. Volumes of 7000 ml per hour without machine downtime is standard for the equipment size mentioned above. Testing of the flower\leaf trichome material prior to extraction is important for product consistency. The results of this batch of trichome material is used in the formulation in creating the end material and product results. A test with 7-10% by weight of THCA/THC and/or CBDA/CBD flower\leaf trichome results combined with 90% by weight seed amount is capable of consistently producing the desired end dosage that manufacturers, consumers, and governments have set as a safe limit. Precise accurate dosing of THC, CBD and other therapeutic cannabinoid components in edibles, drinks, capsules, tinctures, topicals, coffees, suppositories and other offerings is possible using the extract from the process according to a preferred embodiment of the present invention.

The process according to a preferred embodiment of the present invention is an inherently safe process using no flammable solvents or extreme gas pressures. It is also environmentally friendly, with no waste byproducts, effluents or waste stream. Traditional processes create waste from both propellants (hydrocarbons), canisters and leftover plant material; often containing significant amounts of unextracted medicinal content (up to 20% in processes using extraction by $CO_2$). In addition to high-quality oil and medicinal edibles, the process according to a preferred embodiment of the present invention renders leftover plant matter into a commercially valuable high-fibre, high-protein powder with 10% essential fatty acids and 0.2% THCA/THC and or CBDA/CBD (depending upon formulation of flower and seed feedstock). The smallest component by weight and mass is a fine protein\oil sediment extract peanut butter like in texture byproduct named paste as a byproduct as illustrated in FIG. 2.

It is well known that all plant oil-based products have limited shelf-life. Whole food extracts are chemically volatile. Different seeds will yield product of varying perishability. Additions of 0.01% by weight of sage, rosemary and thyme can have beneficial effects on peroxide values and trans fat %, extending shelf life without the incorporation of potentially harmful additives. These additions can also be added to the one step and have positive effects on increasing terpenes and beneficial cannabinoids. Families and genus that fall into this are *Artemesia, Camellia, Catha, Desmodium, Echinacea, Glycine, Helichrysum, Heliopsis, Laminaria, Lepidium, Morinda, Pinus, Piper, Protium, Radula Marginata, Rhodiola, Ruta, Salvia, Syzygium, Trifolium* and *Tuber* Other options for extending shelf-life and medicinal value would include; minerals (coral calcium), bacteria (*Lyngbya cyanobacteria*) and fungus (*Tuber tuberceae*).

Both consumers and manufacturers of natural infused products will significantly benefit from this extraction system, as there are quantifiable, desirable qualities in the product obtained from the process according to a preferred embodiment of the present invention. These desirable qualities do not necessarily exist in extracts created using $CO_2$, butane, water, alcohol or rosin press processes that involve several more complex steps. Additionally, in cases where regulations require oral dosing to test within a certain percentage—usually 5% to 15%—of what the label states, the process according to a preferred embodiment of the present invention is a clearly superior technology in the oral delivery to the North American aging population. The unsurpassed control of end product processing uniformity and the production of efficacious high quality and quantifiable raw materials are substantial advantages.

The testing for THCA/THC and or CBDA/CBD is consistent in both the colloid of infused cannabis oil and the cannabis powder as these chemicals are uniform throughout the end product. The cannabis paste byproduct stream shows oil and protein separation over time (FIG. 2). Testing also produced quantifiable terpenes and other desirable cannabinoids in the processed materials.

The infusion of the process according to a preferred embodiment of the present invention occurs inside a thermodynamic extrusion of continuous temperature & pressure. Cold-pressed Cannabidiol is the product that undergoes decarboxylation.

All illustrations are for the purpose of describing various embodiments of the present invention and are not intended to limit the scope of the present invention. The following descriptions are in reference to FIGS. 1 and 2. According to a preferred embodiment of the present invention, the Entourage Plus Process, is a method for making nutritive edible substances infused with cannabinoids and terpenes. It is an aim of the present invention to provide a consistent and efficacious system which results in the creation of multiple high-potency edible medicinal substances. To accomplish this, a user mixes the whole seed, nut or bean with cannabis plant trichomes (flowers\leaf). The mixture of cannabis plant material is added to edible ingredients, such as hemp seed, flax seed, soy bean, chia seed, poppy seed, canola seed, cacao bean, grape seed, nuts and other nutritive raw materials. In the preferred embodiment of the present invention, the cannabis plant matter mixture can be added to any edible material.

Once the cannabis plant matter is added to the edible material, the formula is placed into a separation machine where it is processed in a continuous stream. In a supplementary embodiment, the mixture is placed into an extrusion machine that separates oil from protein/fibre under pressure and high heat. In this preferred embodiment, the mixture is slightly and briefly heated and subjected to increased pressure during processing. In the preferred embodiment of the present invention, the plant and edible material mixture is subjected to a temperature of up to 180 degrees Fahrenheit during the milling phase with pressures up to 150 psi.

Subjecting the plant and edible material mixture to controlled temperature and pressure during the milling process is also referred to as the Entourage Plus Process. The byproducts resulting from the milling process are edible substances that are infused with THCA/THC and other desired cannabinoid components. The process according to a preferred embodiment of the present invention can also be used to transform THCA into activated THC which can be directly ingested. In addition to extracting/infusing the THCA, the process according to a preferred embodiment of the present invention produces edible materials that have therapeutic benefits derived from the specific heating and pressurization used during processing.

According to a preferred embodiment of the present invention, the process preserves the enzymes amylase, and protease that aid in digestion of the different byproduct streams.

According to another preferred embodiment of the present invention, the process produces a fibrous material which includes trichome plant matter infused with low amounts of THCA/THC and/or CBDA/CBD (approximately 1-2%). When finely ground, this edible cannabis powder resembles commercially available protein powder with the addition of THCA/THC and or CBDA/CBD.

Additionally, the process according to a preferred embodiment of the present invention produces a THCA/THC/^8 THC- and/or CBGA/CBDA/CBD-infused mixture of essential fatty acids and essential oils (terpenes) extracted from the plant matter/edible material mixture. This edible cannabis oil is a colloidal emulsion of essential fatty acids with THCA/THC and/or CBDA/CBD concentrations from 10 to 40 mg/ml, and quantifiable amounts of CBGA, ^8 THC and CBC depending on the formulation, pressure, heat and rpm.

Finally, the process according to a preferred embodiment of the present invention produces a THCA/THC and/or CBDA/CBD infused cannabis paste composed of the materials inserted into the separation machine.

Although the present invention has been explained in relation to its preferred embodiment, it is to be understood that many other possible modifications and variations can be made without departing from the spirit and scope of the invention.

According to a preferred embodiment of the present invention, the process of mechanical extrusion the mixture enters a milling machine such as the one seen in FIG. 4. An auger feeds the mixture (feed stock) where pressure and heat (180° F.) melt the crystallized THCA THC, CBD, CBDA and other cannabinoids and infuse these into the oil seed, nut or bean.

The product produced by the extrusion is separated into 2 streams: a first stream comprising the oil and a second stream comprising the protein and fibre.

FIG. 4 is a side view of a preferred embodiment of a mechanical extruder (1) as used per the present invention. The material (seed or nut and cannabis) is fed into the machine through a feeding hopper (20). The gear unit (10) on the left hand side operates the auger (30) also referred as press screw. The auger is smooth and rotates at 60 rpm. It is 1 foot in length 4 inches in width. The auger has ¼ inch of distance between the inside diameter of the auger housing (40) (also referred to as the press cylinder). 6 channels (cylindrical in shape) 1 inch deep by 1.5 produce the primary pressure before the secondary pressurized area which has a head space of ¼ to ½ inch. The oil is extracted from the press screw at the oil outlet holes (50) and collected in any appropriate container. The oil can then be used for a variety of uses as described in the present application. Preferably, the content of THCA is determined prior to using the extracted oil. The solid product fibrous by-product is extracted at the right hand end of the extruder at the press head (60) where the nozzle (70) provides the outlet for the solid by-product. The solid by-product is collected in a different appropriate container and can be used for a variety of applications as outlined in this description.

A preferred embodiment of the apparatus used in the process of the present invention can produce 100 ml per minute or approximately 220 litres every 24 hours. Preferably, the use of an additional reducer in the $3^{rd}$ stage of pressurization helps constrict the protein fibre resulting in increased oil extraction as a ratio by weight. According to one embodiment of the process, the extraction yields 30 weight % in oil and 70 weight % in protein and fibre.

Subsequent to the extraction, the oil is tested to analyze the yield provided by the mixture of flower and seed of THCA and determine if it was over/under the 30 mg/ml concentration. If the measure of the yield is too low the mixture of seed and flower is adjusted, by increasing the amount by weight of the flower. If the concentration is too high, a reduction in flower weight in the mixture is needed. A typical ratio of flax seed to flower or trim is 90% weight seed (containing 40% oil), 10% weight flower (containing 10% THCA).

According to a preferred embodiment of the present invention, the extracted oils can have one or many of the following medicinal properties; anti-inflammatory properties for treatment of arthritis and lupus; neuroprotective properties for treatment of neurodegenerative diseases; anti-emetic properties for treatment of nausea and appetite loss; anti-proliferative properties noted in studies of prostate cancer; insomnia; treatment of muscle spasms; treatment of pain; use as an insecticide as a topical; and use as an analgesic.

The carrier can provide for different and complimentary profiles and properties as per the following depending on which one is selected. According to a preferred embodiment of the present invention, if the carrier selected is seed-based, the following provides a non-exhaustive list of the potential advantages/health benefits of using such in the extraction process according to the present invention. Flax seeds are a good source of parent omega-3s (better than fish oil) and lignans, super anti-oxidants that help fight cancer. Chia seeds are rich in omega-3 oils, protein, anti-oxidants, calcium, and fiber. Hemp seeds are a certified superfood with cancer and heart disease prevention properties. Hemp seeds are high in protein and fiber, with balanced omega 3 and 6 fatty acids. Sunflower seeds help in the prevention of heart disease and cancer with phytochemicals, folate, Vitamin E, selenium and copper. Pumpkin Seeds are great for the immune system with lots of antioxidants (carotenoids), omega-3 fatty acids and zinc. Sesame seeds are a good source of calcium, magnesium, zinc, fiber, iron, B1 and phosphorus. They can lower blood pressure, and protect against liver damage. They are also linked to prevention of many diseases like arthritis, asthma, migraine headaches, menopause, osteoporosis, and may reduce PMS symptoms. Apricot seeds (aka apricot kernels), apple seeds, and other bitter fruit seeds contain Amygdalin aka Vitamin B17 which has incredibly powerful anti-cancer properties.

According to a preferred embodiment of the present invention, if the carrier selected is nut-based, the following provides a non-exhaustive list of the potential advantages/ health benefits of using such in the extraction process according to the present invention. Almonds can lower cholesterol and help prevent cancer. Walnuts are good for the heart and the brain, and contain ellagic acid a cancer fighting antioxidant. Pecans are a good source of vitamins E and A, folic acid, calcium, magnesium, copper, phosphorus, potassium, manganese, B vitamins, and zinc. And they help lower cholesterol. Brazil nuts are a good source of protein, copper, niacin, magnesium, fiber, vitamin E, and a great source of selenium. Cedar Nuts/Pine Nuts contain vitamins A, B, D, E, P and contain 70% of the human body's required amino acids. Cashews are rich in minerals like copper, magnesium, zinc, iron and biotin. They are a low-fat nut, and like olive oil, they have a high concentration of oleic acid, which is good for the heart.

According to a preferred embodiment of the present invention, the composition obtained from the process of the present invention will be substantially non-psychoactive; it will be a solvent-free clean oil; provide the benefits from THCA/CBDA/CBD; allow a user to take higher doses of THCA than THC; and provide the user with the ability to purchase a product that is similar to other over the counter medicines.

According to a preferred embodiment of the present invention, the carrier and cannabis are mixed in a proportion of 10 kg to 1 kg. The resulting extracted oil from this composition is approximately 3 liters of THCA-containing oil. According to another embodiment of the present invention, cannabis buds and/or flowers are dipped or saturated in vegetable oil (or the like) and then are processed through the extruder.

The process according to the present invention allows for a variety of cannabinoid infused nutritive and therapeutic oils to be produced that include processing with very low levels of decarboxylization allowing for very raw forms of cannabinoids to be captured. This includes THCA. CBDA and CBGA. The latest Health Canada Guidelines also recommend that cannabis be consumed in an edible fashion and be aware of the content and potency of the product. The process creates a nutritive therapeutic oil that is edible and tasty that can also be utilized topically and has independent lab testing to insure the exact beneficial compounds in the products.

The human body is capable of processing ingested raw cannabis, and thus, is able to process extremely large amounts of THCA and CBDA without issue. These acids are then converted into the nutrients it needs through each individual's metabolism and provides the therapeutic benefits available in the particular strain of Cannabis processed with the carrier flax or hemp seed oil. Consuming these cannabinoid acids is important because they help cells communicate with each other via the endocannabinoid system. It may be the key to the prevention of chronic diseases caused by endocannabinoid deficiencies. Endocannabinoid deficiencies are thought to play a major role in the development of medical conditions like: migraines; Irritable Bowel Syndrome; glaucoma; tibromyalgia; Alzheimer's and dementia and potentially for many more ailments currently being researched. Leading researchers have suggested that high doses of raw CBDa and THCa are much more effective than their broken-down counterparts when it comes to their: anti-cancer properties; anti-inflammatory properties; anti-spasmodic properties—Muscle spasms and stomach cramping (IBS); analgesic properties (painkiller that act in various ways on the peripheral and central nervous systems); anti-ischemic properties (ischemia occurs when blood vessels constrict, preventing oxygen from flowing to certain parts of the body); anti-diabetic properties; pH alkalization (reduce and prevent acidic body systems); and anti-oxidant properties.

The following examples are those of individuals suffering from various ailments who have shown improved health after ingesting a preferred composition according to the present invention. The composition made available for testing comprised a 30 mg/ml concentration of THCA obtain A 65 year-old man suffering from knee pain from degeneration ingested 1 ml of a 30 mg/ml composition orally and shown substantial alleviation of the symptoms.

A 67 year-old woman suffering from arthritis in her toe joints used a composition for topical application for a period of 3 months to alleviate the symptoms. She also applied topically the same composition on her nose where she was suffering from skin cancer for the same period of time to reduce the pain.

A 50 year old man suffering from recurring debilitating headaches caused by a bright light ingested 0.5 ml per day orally for a period of 2 months without suffering any headaches.

A 47 year-old man suffering from heartburn ingested 0.5 ml orally. Within 15 minutes, the symptoms were alleviated.

A 38 year-old woman, suffering from painful inflammation of her body, arms and legs from a stillbirth at 6 months. She took 10 ml per day for a period of 1 week. The patient experienced immediate relief and a substantial reduction in swelling According to a preferred embodiment of the present invention, the composition obtained from the process of the present invention will allow a producer to derive a product which is more suitable for medicinal use; the process provides a fast turnaround on oil production; the process results in higher yield than solvent and chemical extraction; and it will also allow for increased product offering.

Although a few embodiments have been shown and described, it will be appreciated to those skilled in the art that various changes and modifications can be made to the embodiments described herein. The terms and expressions used in the above description have been used herein as terms of description and not of limitation, and there is no intention in the use of such terms and expressions of excluding equivalents of the features shown and described or portions thereof, it being recognized that the invention is defined and limited only by the claims that follow.

The invention claimed is:

1. A method for extracting cannabigerol acid from cannabis consisting essentially of:
   a) providing the cannabis consisting essentially of cannabigerol acid, tetrahydrocannabinol acid and cannabidiolic acid;
   b) providing a natural oil selected from the group consisting of flax seed oil, chia seed oil, sunflower seed oil, pumpkin seed oil, sesame seed oil, almond oil, walnut oil, pecan oil, brazil nut oil, cedar nut oil, pine nut oil, and cashew oil;
   c) combining the natural oil and the cannabis to produce a blend;
   d) milling the blend with a screw auger while heating it to produce a liquid blend; and
   e) extracting the cannabigerol acid from the liquid blend.

* * * * *